United States Patent
Tolley et al.

(10) Patent No.: US 7,931,791 B2
(45) Date of Patent: Apr. 26, 2011

(54) METHOD OF DETECTING ANALYTE-BIOMOLECULE INTERACTIONS

(75) Inventors: Luke Tolley, Carbondale, IL (US); Matt McCarroll, Carbondale, IL (US)

(73) Assignee: Southern Illinois University Carbondale, Carbondale, IL (US)

( * ) Notice: Subject to any disclaimer, the term of this patent is extended or adjusted under 35 U.S.C. 154(b) by 665 days.

(21) Appl. No.: 11/923,079

(22) Filed: Oct. 24, 2007

(65) Prior Publication Data

US 2008/0149484 A1 Jun. 26, 2008

Related U.S. Application Data

(60) Provisional application No. 60/862,814, filed on Oct. 25, 2006.

(51) Int. Cl.
*G01N 27/26* (2006.01)
(52) U.S. Cl. ......... 204/459; 204/548; 204/610; 204/612
(58) Field of Classification Search ............ 204/459, 204/548, 610, 612
See application file for complete search history.

(56) References Cited

U.S. PATENT DOCUMENTS

| | | | |
|---|---|---|---|
| 5,376,249 A | 12/1994 | Afeyan et al. | |
| 6,645,733 B1 | 11/2003 | Daksis et al. | |
| 2002/0025576 A1 | 2/2002 | Northrup et al. | |
| 2002/0155106 A1 | 10/2002 | Hammond | |
| 2003/0059811 A1 | 3/2003 | Djaballah et al. | |
| 2004/0029223 A1 | 2/2004 | Karimova et al. | |
| 2004/0058357 A1 | 3/2004 | Soreg et al. | |
| 2004/0096887 A1* | 5/2004 | Ebright et al. | 435/6 |
| 2004/0106129 A1 | 6/2004 | Crook et al. | |
| 2005/0037418 A1 | 2/2005 | Hamalainen et al. | |
| 2005/0064470 A1 | 3/2005 | Rana | |
| 2005/0244821 A1 | 11/2005 | Zik et al. | |

OTHER PUBLICATIONS

Bandilla et al., "Capillary electrochromatography of peptides and proteins", Journal of Chromatography A, 2004, p. 113-129, vol. 1044, No. 1-2.
Montgomery et al., "Dynamic Isoelectric Focusing for Proteomics" Analytical Chemistry, 2006, pp. 6511-6518, vol. 78.
Svensson, "Isoelectric Fractionation, Analysis, and Characterization of Ampholytes in Natural pH Gradients. I. The Different Equation of Solute Concentrations at a Steady State and its Solution for Simple Cases", Acta Chemica Scandinavica, 1961, pp. 325-341, vol. 15.

* cited by examiner

*Primary Examiner* — Alexa D Neckel
*Assistant Examiner* — Jennifer Dieterle
(74) *Attorney, Agent, or Firm* — Polsinelli Shughart PC

(57) ABSTRACT

The invention provides methods for detecting an interaction between an analyte and a biomolecule. The method comprises separating at least one biomolecule according to its isoelectric point in the presence of a given analyte and detecting an interaction between the analyte and a biomolecule using fluorescence anisotropy. The method may further comprise collecting the analyte-biomolecule complex and analyzing the biomolecule.

14 Claims, 13 Drawing Sheets
(5 of 13 Drawing Sheet(s) Filed in Color)

METHOD OF DETECTING ANALYTE-BIOMOLECULE INTERACTIONS

CROSS-REFERENCE TO RELATED APPLICATION

This application claims priority to U.S. Provisional Application Ser. No. 60/862,814 filed on Oct. 25, 2006, which is hereby incorporated by reference in its entirety.

GOVERNMENTAL RIGHTS

This invention was made with Government support under grant number 1 R21 CA120691-01 awarded by the National Institutes of Health. The Government has certain rights in this invention.

FIELD OF THE INVENTION

This invention generally relates to methods for detecting an interaction between an analyte and a biomolecule using dynamic isoelectric focusing techniques and fluorescence anisotropy.

BACKGROUND OF THE INVENTION

Interactions between small molecules (or analytes) and proteins or other biomolecules in a cell are fundamental to biology and medicine. For example, many cells communicate with each other via small molecules that interact with cell membrane receptors. Oftentimes, a pharmaceutical compound is administered to a patient because it has some desirable effect, but little is known about how the pharmaceutical compound mediates the effect. While a variety of techniques have been developed to detect interactions between small molecules and individual biomolecules, there are no reliable techniques for identifying the biomolecule or biomolecules in a cell that interact with a small molecule of interest.

Thus, there is a need for a technique that would detect an interaction between a small molecule of interest and a biomolecule (i.e., detect a complex of the two) and permit isolation of the complex, such that biomolecule of the complex could be further analyzed and identified. Such as technique would be useful in the pharmaceutical industry for the discovery of the mechanism of action of pharmaceutical compounds and potential pharmaceutical compounds. Furthermore, such a technique would be useful in the medical field for identifying which pharmaceutical compound may provide the most desirable effects with the fewest side effects for a particular patient. Similarly, such a technique could be used to determine the effects that a pollutant or contaminant may have on an organism.

SUMMARY OF THE INVENTION

Among the various aspects of this invention, therefore, is a process for detecting interactions between an analyte and a biomolecule, wherein the biomolecule may be isolated and identified.

One aspect of the invention provides a method for separating a biomolecule of interest from other biomolecules in a sample. The method comprises introducing the sample into a separation system comprising a device comprising a first electrode at one end of the device, a second electrode at the opposite end of the device, and at least one additional electrode located between the first and second electrodes. The method also comprises establishing an electric field between the first and second electrodes of the device, such that a pH gradient forms and each biomolecule in the sample migrates to a position within the gradient that is equal to its isoelectric point. Lastly, the method comprises manipulating the position of the biomolecule of interest in the device by adjusting the current applied through the electrodes of the device, such that the shape of the electric field is changed and the pH gradient is shifted.

Another aspect of the invention encompasses a method for detecting an interaction between an analyte and at least one biomolecule. The method comprises introducing the analyte and a sample comprising at least one biomolecule into a separation system comprising a device comprising a first electrode at one end of the device and a second electrode at the opposite end of the device. The method further comprises establishing an electrical field between the first and second electrodes of the device, such that a pH gradient forms and each biomolecule in the sample migrates to a position within the gradient that is equal to its isoelectric point. The analyte is distributed throughout the device. Lastly, the method comprises determining the anisotropy along the length of the device. A non-zero anisotropy value at a particular position along the length of the device indicates the presence of a complex that formed between the analyte and the biomolecule that migrated to that position.

Other aspects and features of the invention are described in more detail herein.

DESCRIPTION OF THE FIGURES

This application file contains at least one drawing executed in color. Copies of this patent application publication with color drawings will be provided by the U.S. Patent and Trademark Office upon request and payment of the necessary fee.

DETAILED DESCRIPTION OF THE INVENTION

Figure 1:
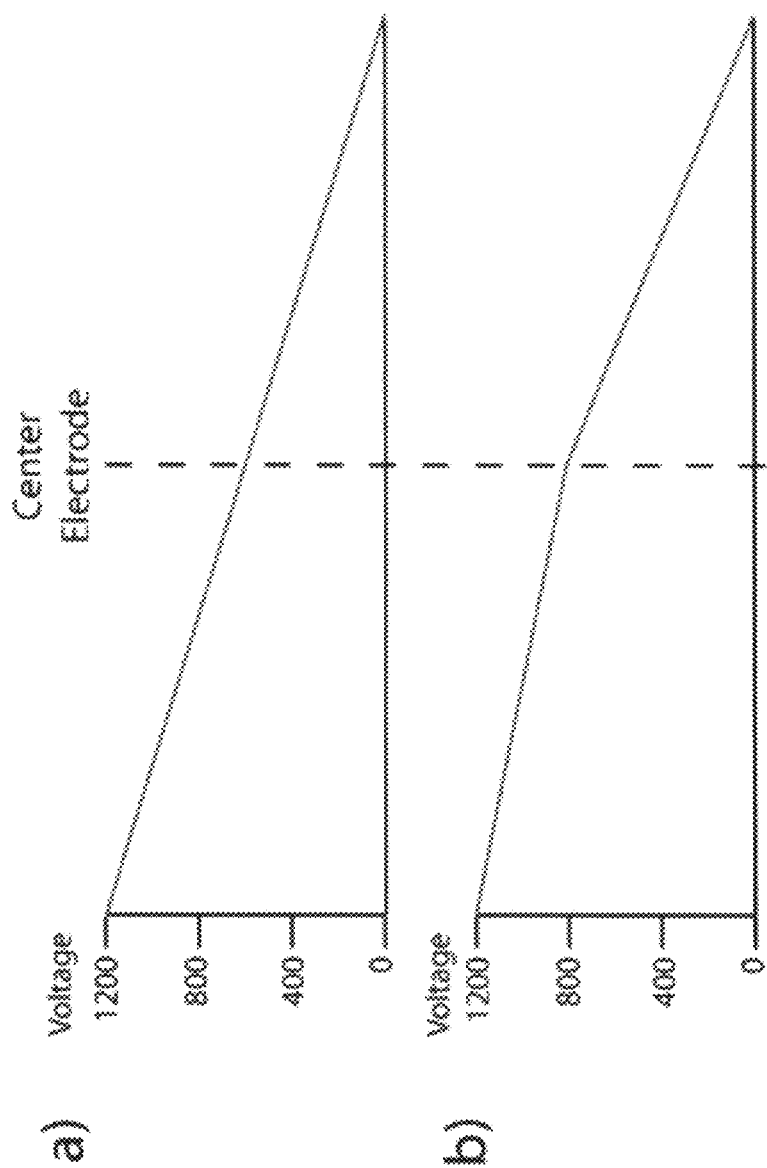
FIG. 1 illustrates the electric field changes in a three-electrode dynamic isoelectric focusing setup. Voltage is plotted as a function of distance. Panel (a) presents an example with equal currents through the whole device. The left electrode has a voltage of 1200 V, the central electrode has a voltage of 600 V, and the right electrode is ground (0 V). Panel (b) presents an example with unequal currents through the whole device. In this situation the voltage of the central electrode was raised to 800 V.

A method has been discovered that detects a molecular interaction between an analyte and a biomolecule. The analyte-biomolecule complex is detected by fluorescence anisotropy. After detection of the analyte-biomolecule complex, the complex may be collected and subjected to further analysis for identification. The method utilizes a dynamic separation method in which biomolecules are separated on the basis of their isoelectric points. The dynamic separation method is conducted in a device comprising additional electrodes, wherein the location of the biomolecule of interest or the analyte-biomolecule complex within the device may be manipulated by adjusting the current introduced via the additional electrodes such that the shape of the electric field is changed and the pH gradient is shifted.

I. Method for Separating a Biomolecule

One aspect of the present invention encompasses a method for separating a biomolecule of interest from other biomolecules in a sample. The method comprises separating the biomolecules in the sample on the basis of their isoelectric points, while providing the ability to manipulate the position of the biomolecule of interest. The method may also be called dynamic capillary isoelectric focusing (dynamic cIEF).

The method of the invention may be performed in a separation system comprising a device comprising a first electrode at one end, a second electrode at the opposite end, and at least one additional electrode located between the first and second electrodes. An electric field is established between the first and second electrodes such that a pH gradient forms and each biomolecule in the sample migrates to a position within the gradient at which its net charge is zero, i.e., the isoelectric point of the biomolecule. The method further comprises manipulating the position of the biomolecule of interest by adjusting the current introduced through the at least one additional electrode to change the shape of the electric filed and shift the pH gradient. When the shape of pH gradient is changed, each biomolecule (i.e., the biomolecule of interest as well as the other biomolecules) migrates to a new position within the gradient that is equal to its isoelectric point. In other words, changing the shape of the electric field within the device may alter the position of the biomolecule of interest within the device.

In general, the device comprises a first electrode at one end of the device, a second electrode at the opposite end of the device, and at least one additional electrode located between the first and second electrodes. Typically, the second electrode is a ground electrode. Typically, the first electrode is connected to an anode compartment that contains a solution of low pH and the second electrode is connected to a cathode compartment that contains a solution of high pH. The device may further comprise a solution of ampholytes, which are low molecular weight molecules capable of ionizing into both anionic and cationic forms. Ampholytes are synthetic, aliphatic polyaminopolycarboxylic acids available commercially whose individual pI values cover a preselected pH range. In general, the pH gradient in the device will range from about pH 3 to about pH 10. In some embodiments, however, a narrower pH range, such as from about pH 6 to about pH 8, may be used.

In one embodiment, the device may comprise a first electrode at one end, a second electrode at the opposite end, and a third electrode located between the first and second electrodes. In another embodiment, the device may comprise a first electrode at one end, a second electrode at the opposite end, a third electrode located between the first and second electrodes, and a fourth electrode located between the third and second electrodes. In yet another embodiment, the device may comprise a first electrode at one end, a second electrode at the opposite end, a third electrode located between the first and second electrodes, a fourth electrode located between the third and second electrodes, and a fifth electrode located between the fourth and second electrodes. A skilled artisan will appreciate that additional permutations are possible in which additional electrodes are located between the first and second electrodes.

Typically, the separation system also comprises at least two high-voltage power sources. In one embodiment, a first high-voltage power source may be connected to the first electrode and a second high-voltage power source may be connected to the third electrode located between the first and second electrodes. In another embodiment, a first high-voltage power source may be connected to the first electrode, a second high-voltage power source may be connected to the third electrode located between the first and second electrodes, and a third high-voltage power source may be connected to the fourth electrode located between the third and second electrodes. In an alternate embodiment, a first high-voltage power source may be connected to the first electrode, a second high-voltage power source may be connected to the third electrode located between the first and second electrodes, a third high-voltage power source may be connected to the fourth electrode located between the third and second electrodes, and a fifth may be connected to the fifth electrode located between the fourth and second electrodes. Additional high-voltage power sources may be connected to additional electrodes located between the first and second electrodes. In each of the above embodiments, each voltage source typically is capable of delivering at least 5000 volts, and more preferably at least 2000 volts.

Application of current from the at least one voltage source forms an electric field between the first and second electrodes. The electric field creates a pH gradient in the device such that each biomolecule migrates to a position in the gradient that is equal to its isoelectric point. In some embodiments, each biomolecule may migrate to its isoelectric position in less than 60 minutes. In other embodiments, each biomolecule may migrate to its isoelectric position in less than 45 minutes. In still other embodiments, each biomolecule may migrate to its isoelectric position in less than 30 minutes.

The shape of the electric field between the first and second electrodes may be changed by adjusting the current introduced through the at least one additional electrode located between the first and second electrodes. For instance, as described above, the device may comprise three electrodes. That is, the first electrode is connected to a first voltage source, the second electrode is used as ground, and the third electrode is connected to a second voltage source. The first and second voltage sources may be used to create a current between the first and third electrodes that is different from the current between the third and second electrodes. This change in the shape of the electric field in turn may change the pH gradient within the device. Accordingly, each of the biomolecules may migrate to a new position in the gradient that is equal to its isoelectric point. In some embodiments, each biomolecule may migrate to a new isoelectric position in less than 20 minutes. In other embodiments, each biomolecule may migrate to a new isoelectric position in less than 10 minutes. In still other embodiments, each biomolecule may migrate to a new isoelectric position in less than 5 minutes.

Figure 3:
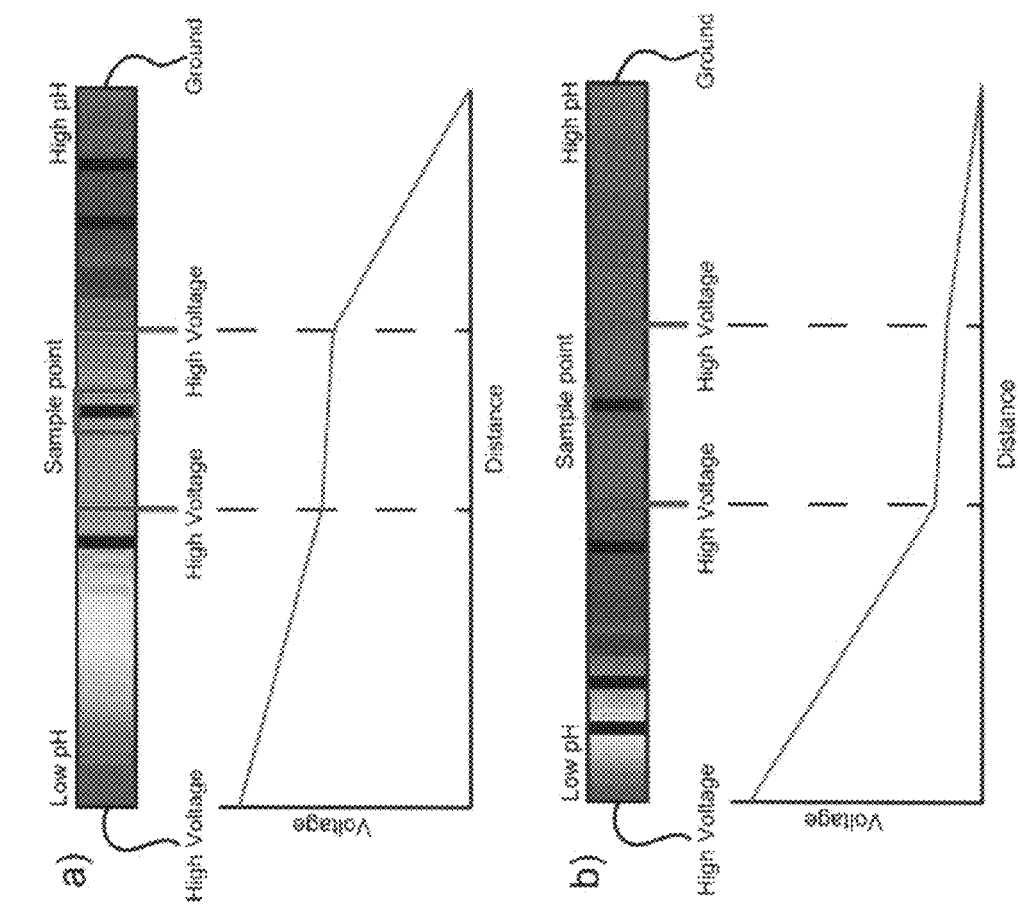
FIG. 3 illustrates the electric fields and pH gradients in a four-electrode system with (a) high voltages and (b) low voltages on the middle electrodes. Note that the voltage difference and, therefore, the bandwidth between the middle electrodes are constant.

In another embodiment, the device may comprise four electrodes, as described above. That is, the first electrode is connected to a first voltage source, the second electrode is used as ground, the third electrode, located between the first and second electrodes, is connected to a second voltage source, and the fourth electrode, located between the third and second electrodes, is connected to a third voltage source. The first, second, and third voltage sources may be used to create a current that between the first and third electrode that is different from the current between the third and fourth electrodes that in turn is different from the current between the fourth and second electrodes. This change in the shape of the electric field in turn may change the pH gradient within the device. For instance, as illustrated in FIG. 3, if the second and third voltage sources deliver a high voltage, then the pH between the second and third electrodes will be low. On the other hand, if the voltage delivered by the second and third voltage sources is decreased, the pH between the second and third electrodes will increase. In a preferred embodiment, the electrical potential difference between the third and the fourth electrodes may range from about 2 to about 20 volts, such that the electric field strength is low between the third and the fourth electrodes. Thus, a biomolecule focused between third and the fourth electrodes will have a constant and controllable bandwidth. Generally speaking, the bandwidth of a focused biomolecule (or an ampholyte) is correlated with the strength of the electric field. For example, a low electrical field strength produces a broad bandwidth, whereas a high electrical field strength produces a narrow bandwidth.

In general, the device may have an observational port located between the first and second electrodes. In some embodiments, the observational port may coincide with a collection port. The collection port typically allows a portion of the solution to be removed from the device. In one embodiment, the device may comprise three electrodes as described above, and the collection port may be located adjacent to the middle third electrode. That is, the collection port may be to the left or to the right of the third electrode. In another embodiment, the device may comprise four electrodes as described above, and the collection port may be located between the third and fourth electrodes. In still another embodiment, the device may comprise five electrodes as described above, and the collection port may be located between the third and fourth electrodes or, alternatively, the collection port may be located between the fourth and fifth electrodes. In yet another embodiment in which the device comprises five electrodes, the device may comprise two collections ports. In this case, a first collection port may be located between the third and fourth electrodes and a second collection port may be located between the fourth and fifth electrodes.

The focused biomolecule of interest may be positioned over the collection port by adjusting the current introduced into the device through the additional electrodes located between the first and second electrodes. If the biomolecule of interest is to be removed from the device, it is most advantageous for the width of the focused biomolecule to be about the same width as the width of the fraction collected from the device through the collection port. In one embodiment, the width of the fraction collected from the device through the collection port may be about less than about 0.1 pH units. In another embodiment, the width of the fraction collected from the device through the collection port may be less than about 0.05 pH units. In yet another embodiment, the width of the fraction collected from the device through the collection port may be less than about 0.01 pH units.

After collection of a fraction comprising the biomolecule of interest, the fraction may be analyzed, using techniques known in the art, to determine the identity of the biomolecule or biomolecules in the fraction. For example, liquid chromatography, gas chromatography, ion mobility spectrometry, mass spectrometry, matrix-assisted laser desorption ionization mass spectrometry, electrospray ionization mass spectrometry, or a combination thereof may be used to determine the identity of the biomolecule(s).

In some embodiments, the device may be a microfluidic platform. Microfluidic platforms are well known in the art, for instance, see J Chromatogr A. 2004 Jul. 30; 1044(1-2):113-29. Accordingly, the device may be a channel or a microchannel. The channel or microchannel may be made of silica, metal, or a polymer. In preferred embodiments, the device may be a capillary. The capillary may be a silica capillary, a fused silica capillary, a silane derivatized capillary, a plastic capillary, or another suitable capillary well known to those of skill in the art. Generally speaking, the device may be between about 2 cm and about 20 cm long. In one embodiment, the device may be between about 3 cm and about 15 cm long. In another embodiment, the device may be between about 5 cm and about 15 cm long. In yet another embodiment, the device may be between about 7 cm and about 12 cm long. In still yet another embodiment, the device may be about 10 cm long. The device may have internal dimensions between about 200 µm and about 50 µm. In one embodiment, the internal dimensions may be between 150 µm and about 80 µm. In another embodiment, the internal dimensions may be between about 125 µm and about 75 µm. In yet another embodiment, the internal dimensions may be about 100 µm.

The device may have rounded surfaces, or flat surfaces. In one embodiment, the device may be circular. In another embodiment, the device may be rectangular. In yet another embodiment, the device may be linear. The device may be coated or treated with surfactant and hydrophilic polymers to reduce or eliminate electroosmotic flow. For example, the device may be coated with hydroxypropyl cellulose, as detailed in the examples. The device may or may not have a polyimide coating. In one embodiment, the polyimide coating may be removed from a short section of the device. In another embodiment, the polyimide coating may be removed from a large section of the device. In yet another embodiment, the polyimide coating may be removed from the entire device.

The separation system may further comprise detection means. Detection means may comprise a visualization means, such as an inverted, confocal, or a epifluorescence microscope with appropriate optics, objectives, filters, light sources, such as ultraviolet, visible light, or laser light sources, and capture means, such as a CCD camera, a video monitor, or a digital camera.

The biomolecule of interest may be a protein, a peptide, a nucleic acid, a lipid, a carbohydrate, an antibody, a microorganism, a prion, or a virus. In a preferred embodiment, the biomolecules to be separated are proteins. The sample comprising the biomolecule of interest may be a purified preparation, a synthetic reaction, an enzymatic reaction, a cell lysate, a cancer cell lysate, a cell culture supernatant, or a body fluid, such as whole blood, serum, plasma, cerebrospinal fluid, tears, urine, feces, saliva, vaginal fluid, nipple aspirate/lactation fluid, semen, perspiration, peritoneal fluid, and lavages. The number of biomolecules that may be separated by the method can and will vary, depending upon the source of the sample. In one embodiment, more than 2 biomolecules may be separated. In another embodiment, more than 10 biomolecules may be separated. In yet another embodiment, more than 100 biomolecules may be separated. In an alternate embodiment, more than 1000 biomolecules may be separated. In another alternate embodiment, more than 5000 biomolecules may be separated.

II. Detecting an Interaction Between an Analyte and a Biomolecule

Another aspect of the present invention provides a method for detecting an interaction between an analyte and at least one biomolecule. The method comprises introducing the analyte and a sample comprising the at least one biomolecule into a separation system comprising a device comprising a first electrode at one end and a second electrode at the opposite end of the device. The method comprises establishing an electrical field between the first and second electrodes such that a pH gradient forms and each biomolecule in the sample migrates to a position within the gradient that is equal to its isoelectric point. Typically, the analyte is uniformly distributed throughout the device. The method further comprises determining the anisotropy along the length of the device, wherein a non-zero anisotropy value at a particular position along the length of the device indicates that an analyte-biomolecule complex has formed at that location.

The separation of biomolecules on the basis of their isoelectric point was detailed above. In some embodiments, the device may comprise at least one additional electrode located between the first and second electrodes, as detailed above. In a preferred embodiment, the device comprises a third electrode located between the first and second electrodes and a fourth electrode located between the third and second electrodes. Thus, interactions between analytes and biomolecules may be detected using dynamic cIEF in combination with anisotropic measurements. Furthermore, the location of the analyte-biomolecule complex may be manipulated by changing the shape of the electric field by adjusting the current introduced through the third and fourth electrodes, as detailed above. In other embodiments, the device further comprises a collection port, as detailed above. In a preferred embodiment, the device comprises third and fourth electrodes located between the first and second electrodes and a collection port located between the third and fourth electrodes. Thus, the analyte-biomolecule complex may be positioned over the collection port by manipulating the shape of the electric field, and the complex may be removed from the device for further characterization, as detailed above.

Generally speaking, the analyte is a small molecule. Non-limiting examples of suitable analytes a pharmaceutical compound, a potential pharmaceutical compound, a drug, a ligand, an enzyme substrate, a second messenger, a hormone, a neurotransmitter, a nucleic acid, a small RNA molecule, an antigen, an environmental contaminant, a toxin, a chemical moiety, a fatty acid, a steroid, a carbohydrate, an amino acid, a peptide, a polypeptide, a microbe, a virus, or a fragment thereof.

The analyte may or may not be naturally fluorescent. An example of a naturally fluorescent analyte is the cox-2 inhibitor rofecoxib. If the analyte is not naturally fluorescent, a fluorophore may be attached to the analyte. Suitable fluorophores include, but are not limited to, fluorescein and its derivatives, rhodamine and its derivatives such as ROX and Texas Red; the Cy dyes such as Cy3 and Cy5 (Amersham Biosciences, Pittsburgh, Pa.); and the Alexa fluor dyes (Molecular Probes/Invitrogen, Carlsbad, Calif.). Methods of attaching fluorophores to analytes are well known in the art.

The analyte may also be charged or uncharged. If the charge of an analyte is affected by pH, it is desirable that the method of detecting analyte and biomolecule interactions be performed at least twice. First, at least a pH range where the analyte is not charged, and second, at a pH range where the analyte is charged.

The biomolecule(s) and the sample comprising the biomolecule(s) were detailed above.

Figure 9:
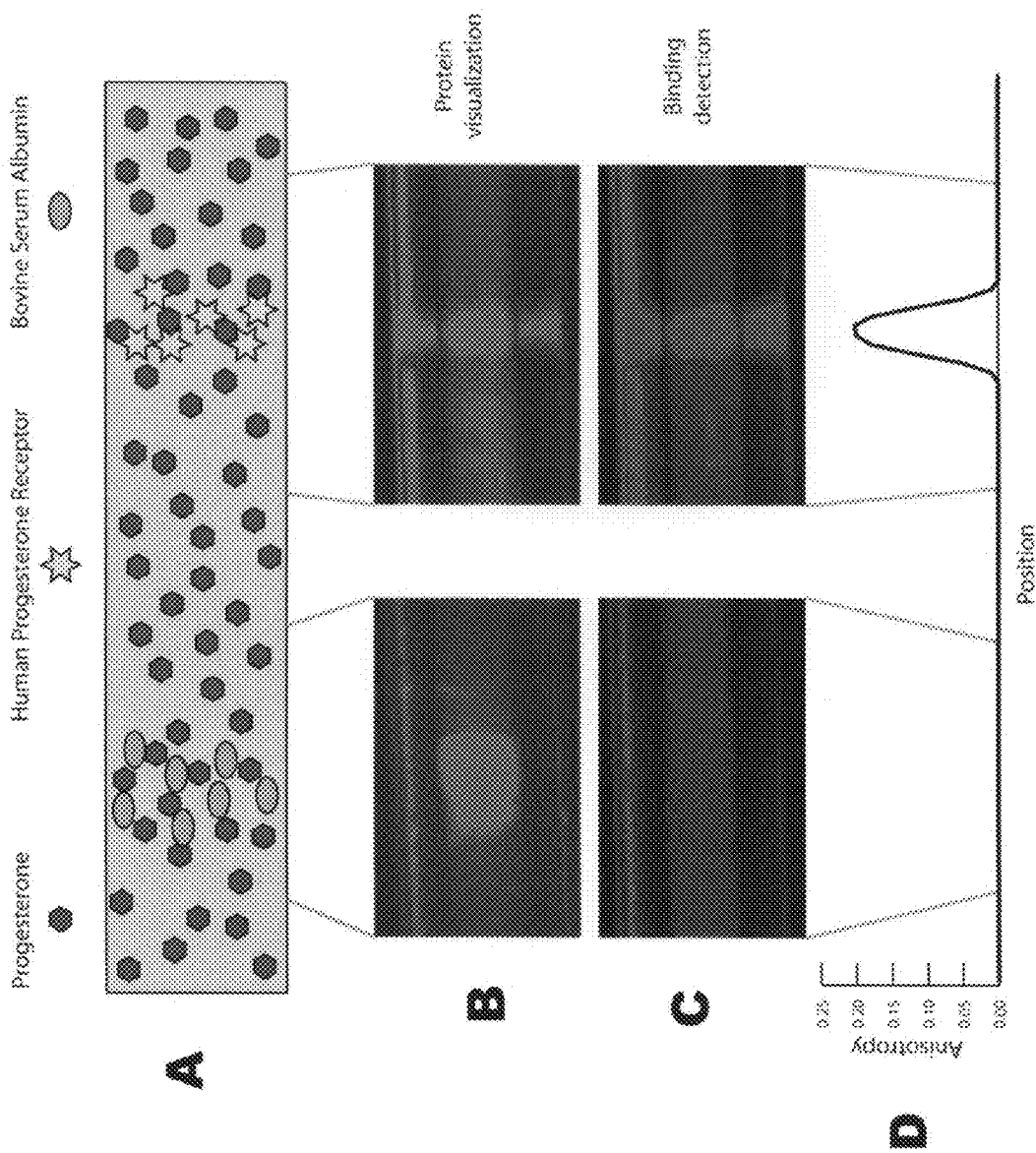
FIG. 9 depicts the expected and observed anisotropy response between progesterone and two proteins in a capillary. Panel (A) presents the expected results. Panel (B) shows the bands of the two focused proteins as visualized by rhodamine fluorescence. Panel (C) illustrates binding of the fluorescein-labeled ligand to the receptor. Panel (D) illustrates high anisotropy values in the region containing the ligand-receptor complex.

After separation of the biomolecule(s) using the methods described in section (I), the anisotropy of the analyte may be used to detect interactions between the analyte and at least one biomolecule. Typically, the molecule interaction will be measured via fluorescent anisotropy. Accordingly, the analyte will be fluorescent. Generally speaking, the measurement of fluorescent anisotropy involves the determination of fluorescence intensity of the parallel and perpendicular component of the fluorescence emission, following excitation with vertically polarized light. Anisotropy values may be calculated or approximated by methods well known in the art. These values may be graphically plotted. For example, the calculated or approximated anisotropy may be plotted as a function of pH, or the calculated or approximated anisotropy may be plotted versus distance along the length of the device, as illustrated by FIG. 9D. A non-zero value for anisotropy at a particular pH value (or location in the device) generally indicates an interaction between the analyte and the biomolecule that migrated to that pH value (or location). See Examples 6 and 7 for more details.

The position of a focused band (i.e., an analyte-biomolecule complex) that has a non-zero anisotropy value, whether calculated or approximated, may be manipulated within the device, as described above. In particular, a focused band having a non-zero anisotropy may be manipulated within the device so as to position the analyte-biomolecule complex over a collection port. This allows collection of the analyte-biomolecule complex via the collection port. The collected fraction comprising the analyte-biomolecule complex may be further analyzed to determine the identity of the biomolecule that interacted with the analyte. Suitable methods of analysis were presented above. After removal of a first analyte-biomolecule complex, a second analyte-biomolecule complex may be refocused within the device, position over the collection port, and removed for analysis. One of skill of in the will appreciate that this could be repeated many times and many fractions could be collected for analysis.

The above-described method may be used to detect, isolate, and identify biomolecules that interact with a given analyte. In particular, the method may be used to detect and identify biomolecules that interact with a pharmaceutical compound or a potential pharmaceutical compound. For example, the method may be used to determine the protein(s) that interact with a pharmaceutical compound or a potential pharmaceutical compound. Proteins from a wide variety of sources may be evaluated with the given method. This may allow determination of the mode of action of a particular pharmaceutical compound.

In other embodiments, the above-described method may be used to detect, isolate, and/or identify a receptor that interacts with a given ligand. The ligand may be a hormone, a small peptide, a small molecule, an amino acid, a small carbohydrate, a nucleoside, and so forth. The method of the invention may isolate and identify the receptor that binds the ligand more readily than competitive binding assays and traditional purification techniques. In another embodiment, the method may be used to detect, isolate, and/or identify an enzyme that interacts with a given substrate. For example, the substrate may be a pharmaceutical compound as described above. Furthermore, because the biomolecule(s) are separated on the basis of isoelectric point under non-denaturing conditions, the enzyme biomolecule may retain enzyme activity after removal of the complex from the device, such that enzyme assays may be performed. In still another embodiment, the method may be used to detect, isolate, and/or identify a transcription factor or a protein that interacts with a nucleic acid. The nucleic acid may be a promoter sequence, an enhancer sequence, a regulatory sequence, a 3' UTR sequence, a small RNA, and so forth. In further embodiments, the method may be used to detect and analyze antigen-antibody interactions, virus-protein interactions, prion-protein interactions, antibiotic/substrate-microbe interactions, eukaryotic cell membrane protein-microbe interactions, and so forth.

In another iteration of the above-described method, the anisotropy detection system may be constructed to measure the anisotropy of the entire device at once. Accordingly, a pattern of the analyte-biomolecule complexes within the device may be determined based upon the regions of non-zero anisotropy. Thus, each sample would have a "binding pattern" that corresponds to the pattern of analyte-biomolecule complexes along the length of the device. In this embodiment, the analyte-biomolecule complexes generally are not removed from the device, but rather "binding patterns" are generated and binding patterns between samples are compared. For example, binding patterns between different samples may be used for comparing interactions between a pharmaceutical compound with the biomolecules present in different samples. Accordingly, the binding pattern between a given pharmaceutical compound and the biomolecules in one sample (e.g., brain lysate) may be compared to the binding pattern obtained with that pharmaceutical compound and a second sample (e.g., heart lysate). Such a comparison may be used to detect a previously unknown interaction between the pharmaceutical compound and a biomolecule in one of the samples. For example, a biomolecule that interacts with the given pharmaceutical compound in one tissue sample but not other tissue samples may be an indicator of a possible side effect of the pharmaceutical compound. In the above example, an additional, minor analyte-biomolecule complex in the heart sample may indicate that the pharmaceutical compound has cardiac-specific side effects. Having such information prior to animal testing may facilitate the development of new pharmaceutical compounds. For example, a large number of derivatives of the pharmaceutical compound may be synthesized and screened with this method until a derivative is found that does not exhibit the additional, minor interaction.

Additionally, the binding pattern of a first analyte in a sample may be compared to the binding pattern of a second analyte in the same sample. Such a comparison may be used, for instance, to compare the interactions of two different pharmaceutical compounds or potential pharmaceutical compounds with biomolecules in a given cell lysate. This comparison may be useful to determine how a particular pharmaceutical compound may affect an individual or to determine which pharmaceutical compound may have the fewest side effects in an individual. Such an analysis may be useful for treating cancers, since many cancers are caused by mutations that are unique to the individual.

In yet another alternative embodiment, the binding pattern for a given analyte in a sample derived from one organism may be compared to the binding pattern for the same analyte in the same type of sample derived from a second organism. For example, the binding pattern for a given pharmaceutical compound in a sample derived from the heart of one patient may be compared to the binding pattern for the same pharmaceutical compound in a sample derived from the heart of a different patient. Such a comparison may be useful to determine if a particular pharmaceutical compound will be effective for a given patient. Such an analysis also may be particularly useful for patients with cancer. A binding pattern for a particular anti-cancer pharmaceutical may be evaluated to determine if a given patient will respond to the anti-cancer pharmaceutical. Currently, such an evaluation is made by administering the pharmaceutical agent and observing the effects on the tumor, which may take weeks to months. Advantageously, the present invention provides a faster alternative.

Definitions

To facilitate understanding of the invention, a number of terms are defined below:

As used herein, the term "analyte" generally refers to a small molecule. The small molecule may be a pharmaceutical compound, a potential pharmaceutical compound, a drug, a ligand, a substrate, a second messenger, a hormone, a neurotransmitter, a nucleic acid, a small RNA molecule, an antigen, a fatty acid, a steroid, a carbohydrate, an amino acid, a peptide, a polypeptide, an environmental contaminant, a toxin, a chemical moiety, a microbe, a virus, or a fragment thereof.

The term "biomolecule," as used herein may refer to a protein, a peptide, a nucleic acid, a lipid, a carbohydrate, an antibody, a microorganism, a prion, or a virus.

As various changes could be made in the above compounds, complexes, and methods without departing from the scope of the invention, it is intended that all matter contained in the above description and in the examples presented below, shall be interpreted as illustrative and not in a limiting sense.

EXAMPLES

The following examples illustrate various embodiments of the invention.

Examples 1-5

Characterization of Dynamic Isoelectric Focusing Theory

Dynamic isoelectric focusing (dynamic IEF) is similar to capillary isoelectric focusing (cIEF) in that it focuses proteins on the basis of their isoelectric point by establishing a pH gradient using ampholytes and an electric field. Although the pH gradient and the electric field in cIEF are constant, giving each focused protein in the sample a fixed position, dynamic IEF moves the pH gradient through manipulation of the electric field. This enables control over each protein's position and focused width. By changing the electric fields during a separation, focused proteins can be brought to a fixed sample point for collection and further analysis by chromatography or mass spectrometry, for instance. The dynamic control of each protein's position overcomes the major disadvantage of cIEF, which is the difficulty in interfacing to other techniques, while providing all of the advantages of cIEF.

Dynamic IEF establishes a pH gradient in a capillary using carrier ampholytes and an electric field, as does standard cIEF. Whereas cIEF uses a single high-voltage power supply connected to an electrode at one end of the capillary, dynamic IEF incorporates additional power supplies connected to additional electrodes along the capillary length. These power supplies permit the shape of the electric field within the capillary to be changed. The effects that a different electric field shape has on the pH gradient within the capillary can be understood using fundamental IEF equations introduced by Svensson (Acta Chem. Scand. 1961, 15, 325-341).

The base differential equation that determines the concentration distribution of an ampholyte is $$\frac{Cui}{q\chi} = D\frac{dC}{dx} \quad (1)$$

where C is the ampholyte concentration, u is the electrophoretic mobility in cm$^2$ volt$^{-1}$ s$^{-1}$, is the current in amperes, q is the cross-sectional area of the capillary in cm$^2$, $\chi$ is the conductance of the buffer in $\Omega^{-1}$ cm$^{-1}$, D is the diffusion coefficient in cm$^2$ s$^{-1}$, and x is the distance along the separation space. Each side describes the mass flow per second and cm$^2$, with the left side being mass flow due to migration in the electric field and the right side, due to diffusion. In the same reference, a solution to this differential equation gives the concentration profile of a focused analyte as $$C(x) = C_0 \exp\left(-\frac{pix^2}{2qxD}\right) \quad (2)$$

where p is the change in electroosmotic mobility with distance (du/dx). This equation indicates that the peak has a Gaussian shape, with spread about the isoelectric point given by $$\sigma = \sqrt{\frac{qxD}{pi}} \quad (3)$$

Since an increase in the applied voltage increases both i and p, the width of each ampholyte band changes linearly with respect to electric field strength.

During dynamic IEF, the electric fields encountered by the ampholytes are changed during the analysis, with the goal of controlling the shape of the pH gradient. When the electric fields change, the ampholyte peaks will correspondingly change their width, as eq 3 indicates.

A dynamic IEF setup is illustrated in FIG. 1a using voltages of 1200 (voltage 1), 600 (voltage 2), and 0 (ground), with voltage 2 being in the middle of the capillary. The electric field strength will be constant across the whole capillary. Since the voltage drop between voltages 1 and 2 is the same amount as that between voltage 2 and ground, the current in both parts of the capillary is the same. This means that voltage 2 does not actually supply any current to the capillary. The ampholyte bandwidths will also be the same along the capillary length. If the value of voltage 2 is raised to 800 V, then a piecewise linear electric field will form in the capillary, as shown in FIG. 1b. There is a voltage drop of 400 V from voltage 1 to voltage 2 and a 800 V drop from voltage 2 to ground. The current from voltage 1 to voltage 2 is, therefore, much less than the voltage 2 to ground. The extra current flowing to ground comes from voltage 2 and has a large effect on the ampholytes.

Figure 2:
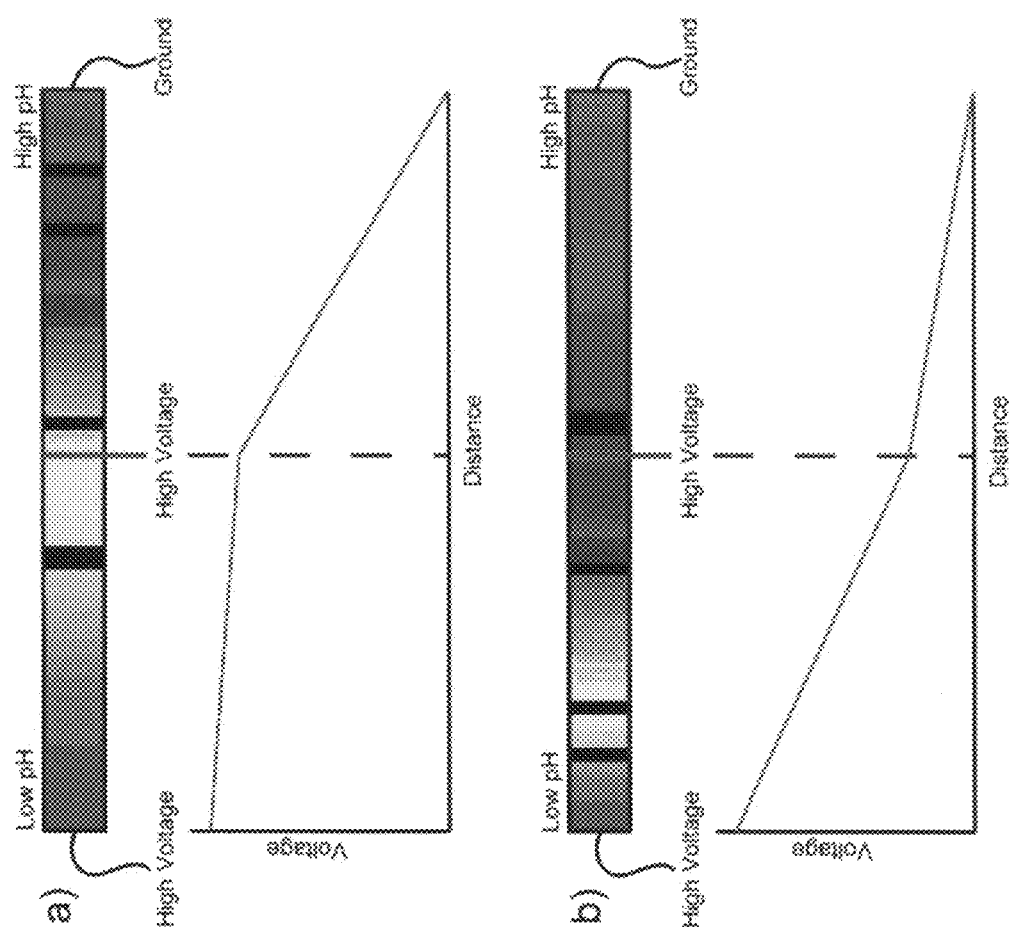
FIG. 2 illustrates the electric fields and pH gradients in a three-electrode system with (a) a high voltage and (b) a low voltage on the middle electrode.

A simple implementation of dynamic IEF is provided in FIG. 2. It uses only one additional power supply, so it is referred to as a three-electrode system. This simple system allows for dynamic mobilization to be observed and tested. Though the theory and implementation of dynamic IEF can be validated using this setup, it does not allow for easy sample collection or interfacing to additional separation methods. A fixed sampling point could be integrated, but it would not provide consistent collection efficiency. Imagine that a sample collection valve is placed in the system to the right of the middle electrode in FIG. 2a. The band collected under conditions depicted in FIG. 2a will be very narrow due to the steep electric field and pH gradient. However, when the conditions in 2b are reached, then the band at the valve will be much broader. If all other conditions remain constant, then the width of each band is based on the electric field strength, as was shown in eq 3. Since the change in voltage and pH with distance is much lower in FIG. 2b than in 2a, the band will be broader. This variance in field strength and the corresponding change in bandwidth decreases the usefulness of a three-electrode system. A four-electrode system can solve this problem, as illustrated in FIG. 3.

In a four-electrode system, there are two additional electrodes in the capillary that have a fixed observation or sampling point between them. Their voltages are adjustable, but the voltage difference between them generally remains constant. A fixed voltage differential provides a constant electric field strength at the sampling point, meaning that the bands focused between these electrodes will also have a constant and controllable width. The total voltage at the sampling point will change, changing the pH, but it is the electric field strength that determines the width of the band. FIG. 3a shows the collection of a protein with a low pI, and 3b shows the collection of a high pI. The bandwidths at each end of the capillary will change with changing conditions, but the center section will always encounter constant widths.

Experimental Methods for Examples 1-5

Reagents and Chemicals. Acetic acid, ammonium acetate, hydroxypropyl cellulose (HPC, av MW 100 000), HPLC grade dimethyl sulfoxide (DMSO), HPLC grade water, PTFE tubing, horse heart myoglobin, R-cyano-4-hydroxycinnamic acid (CHCA), universal indicator solution, and phosphate-buffered saline (PBS, pH 7.4) were obtained from Fisher Scientific (Fairlawn, N.J.). Ampholytes (Pharmolyte 3-10 for IEF) and calibrated protein buffer (broad range, pH 3-10) were obtained from Amersham Biosciences (Piscataway, N.J.). Tetramethylrhodamine-5-(and -6)-isothiocyanate (TRITC) was obtained from Invitrogen (Carlsbad, Calif.).

Sample Preparation. A solution of fluorescently labeled proteins was prepared according to the manufacturer's protocol. Briefly, a standard buffer of proteins with known isoelectric points was dissolved in PBS at 6 mg/mL. TRITC was dissolved in DMSO at 1 mg/mL. The TRITC solution was added to the protein sample and incubated in the dark for 2 h. The labeled protein solution was then filtered through a 100-kDa centrifugal filter (Millipore, Bedford, Mass.) to remove any protein aggregates. Finally, the unbound TRITC was removed from the labeled proteins by filtering through a 10-kDa centrifugal filter (Millipore) and using the retained portion.

Samples for analysis by matrix-assisted laser desorption ionization mass spectrometry (MALDI-MS) were mixed with 1 mg/mL CHCA matrix solution in a sample/matrix ratio of 1:8. After mixing, 0.5 µL of this solution was spotted onto a MALDI target plate and allowed to dry.

Instrumentation. The high-voltage power supply used was fabricated in-house. It contains five 10-kV supplies (Ultravolt, Ronkonkoma, N.Y.), each of which is individually controlled by a computer using LabView (National Instruments, Austin, Tex.). Fluorescence emission was viewed using an inverted microscope with a 10× long-range objective with excitation at 544 nm and emission at 572 nm. A digital video camera was attached to the microscope for recording images and video. The MALDI-MS used was a 4700 TOF-TOF (Applied Biosystems, Framingham, Mass.) with a pulsed nitrogen laser set at an intensity of 4000. It was operated in linear mode with a focus mass of 17 000 Da.

Focusing Capillaries. Fused-silica capillaries of 75 µm i.d., 360 µm o.d. (Polymicro, Phoenix, Ariz.) were coated with hydroxypropyl cellulose by filling them with a 5% HPC solution and then baking them at 200° C. for 45 min. This treatment effectively eliminated electroosmotic flow in the capillary. Each capillary was filled with either 1% ampholyte solution or a protein sample solution in 1% ampholytes prior to use.

Electrical Connections. To perform dynamic IEF, electrical connections must be made to different locations inside the capillary, and this must be done without causing leakage of the ampholyte solution and without forming bubbles in the capillary. To accomplish this, a PTFE tube with an inner diameter of 0.014 in. (~356 µm) was carefully cut partway through, orthogonal to its length. The capillary was then cut, and the two sections were inserted into the tubing until the junction was 1 mm from the cut. The cut section of the tubing was then inserted into a small acrylic reservoir that contained a platinum electrode connected to the high-voltage power supply. The lack of pressure coupled with the offset between the cut and the capillary union permitted an electrical connection while preventing fluid leakage.

Example 1

Proof-of-Concept with PTFE Tubing

Figure 4:
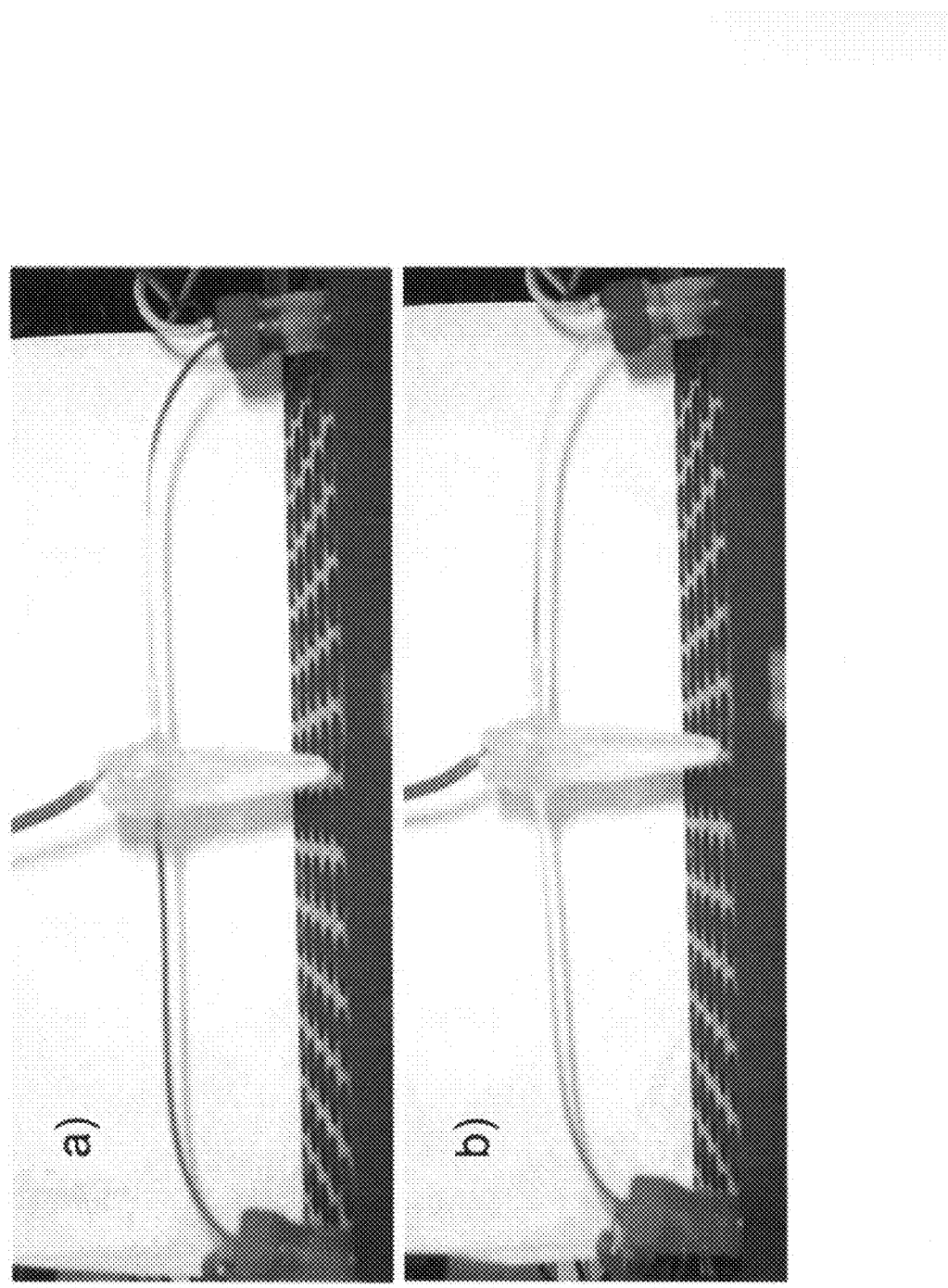
FIG. 4 presents photographs of dynamic isoelectric focusing performed in a polymer tube with universal indicator added to the ampholyte buffer. Panel (a) depicts the initial pH gradient after the focusing with voltages of 2200, 2195, and 0, on the left, middle, and right electrodes, respectively. Panel (b) depicts the refocused pH gradient after refocusing with voltages of 2200, 1100, and 0, on the left, middle, and right electrodes, respectively.

Proof-of-concept tests were performed using PTFE tubing with an i.d., of 0.02 (~528 µm) in a three-electrode configuration. The tubes were filled with universal indicator and a 3% ampholyte solution. Photographs of this setup are seen in FIG. 4. The relatively large tubing has several disadvantages, such as excess heating, siphoning, and eddy currents, but the size made it possible to easily see the pH gradients as they formed and were then moved. The anode contained 0.2 M acetic acid; the cathode, 0.5% ammonium hydroxide; and the center vial, 3% ampholyte. FIG. 4a shows the initial focusing conditions with voltages of 2200, 2195, and 0 V. As expected, the pH gradient forms between the center electrode and ground, and the high voltage section is completely acidic. The center voltage was then dropped to 1100 V, and the gradient was moved so that a neutral pH was present in the center, as shown in FIG. 4b. The refocusing took ~10 min. Although this experiment did not assess the performance of dynamic IEF for protein separations, it did verify the concept of dynamically controlling the pH gradient through the electric fields.

Example 2

Monitoring Current Profiles

Figure 5:
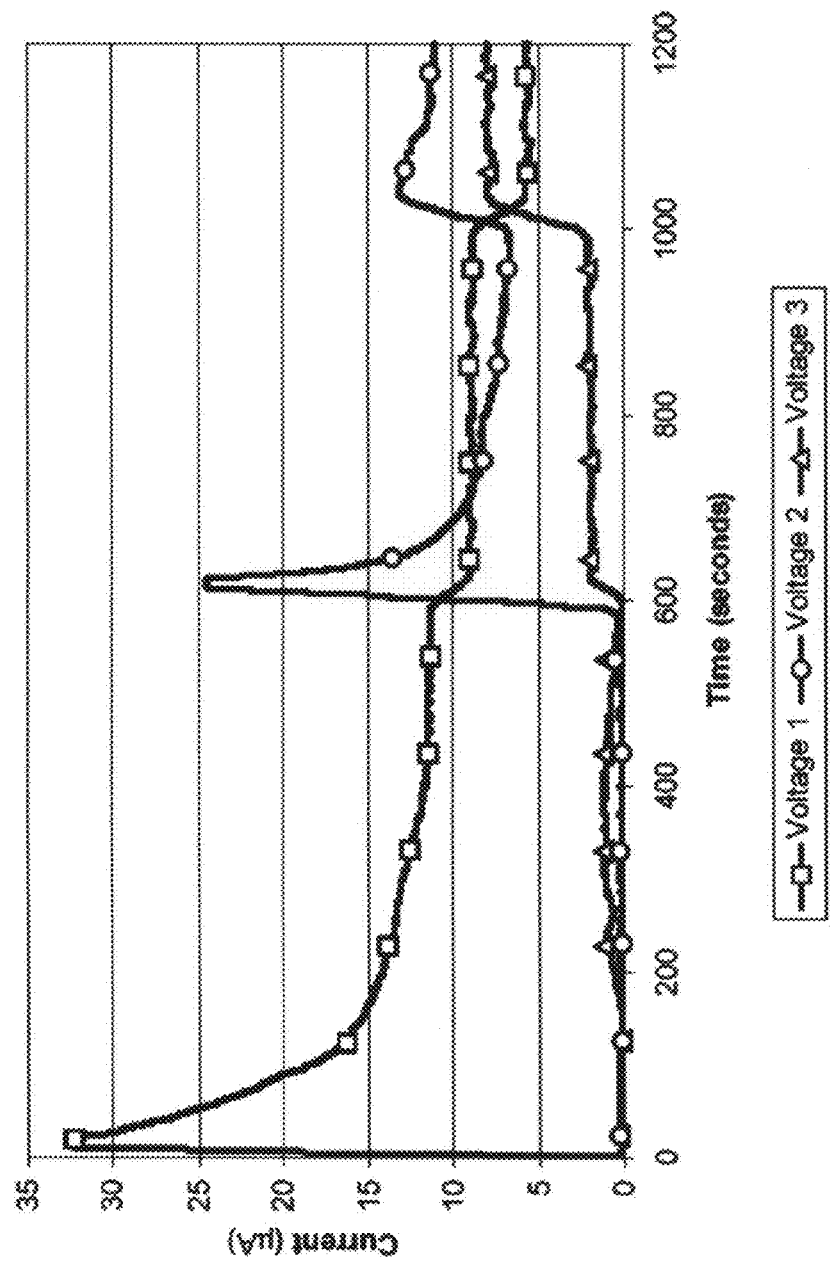
FIG. 5 illustrates current traces from a four-electrode system undergoing focusing with mobilization steps occurring at 600 and 1000 sec.

Another means of monitoring the focusing and refocusing process is to monitor the currents from the power supplies. In isoelectric focusing, the total amount of current in the system drops exponentially as the ampholytes and proteins migrate to their isoelectric point. Dynamic isoelectric focusing should exhibit such a current drop every time the voltage is changed as the ampholytes migrate to their new positions. This expected behavior was observed in the voltage and current traces of a four-electrode system with a total capillary length of 18 cm, consisting of sections of 7, 4, and 7 cm, respectively. The anode contained 0.2 M acetic acid; the cathode, 0.5% ammonium hydroxide; and each of the center vials had 3% ampholyte. Initial focusing was performed, followed by several mobilization steps. The recorded current trace is shown in FIG. 5.

The starting voltages were 2400, 200, and 180 V for voltages 1-3. The final reservoir was always grounded. The initial focusing occurred mainly between voltages 1 and 2 because of the large voltage differential, and the focusing took approximately 9 min. The proteins were considered focused when the current from voltage 1 reached its background level of ~4 µA/kV. Once the initial focusing was complete, voltages 2 and 3 were increased to 1200 and 1180 V to refocus the proteins to a different location inside the capillary. The current from voltage 2 rose and then decayed, indicating the refocusing that occurs. Focusing was performed a third time by increasing voltages 2 and 3 to 2100 and 2080 V. Total analysis time was ~20 min.

Example 3

Testing pH in Sampling Region

Since there could be other processes responsible for the behavior of the currents, the pH in the center section of capillary was directly measured under similar conditions. Voltage 1 was set to 2000 V with a buffer solution of pH 3. The ground electrode had a buffer with a pH of 10, giving a pH span of 7 units. Initial focusing was performed by setting voltage 1 to 2000 V and the rest of the voltages to ground. This caused the entire pH gradient to form between voltages 1 and 2. After focusing, voltages 2 and 3 were increased, and the system was allowed to refocus. The voltages were then disconnected, and the center section of capillary (~4 cm in length) was removed. The liquid in this section was added to 50 µL of universal pH indicator solution. The center capillary was refilled with ampholyte solution and reinserted. The voltages were reconnected, and voltages 2 and 3 were increased, changing the pH within the center section. This whole process was repeated nine times, as listed in Table 1, with center voltages ranging from 15 to 89% of voltage 1, corresponding to pH values from 3.8 to 9. The expected pH at each center electrode was calculated by dividing the electrode voltage by the total voltage and then multiplying by the pH span of the separation. This result indicates the number of pH units between the electrode and ground. The final step was to subtract this value from the pH at the ground electrode. The color produced after each mobilization step matched the expected indicator color, confirming that the pH present at the sampling point is directly controlled by the electric field and can be changed as desired.

TABLE 1

Changes in pH in a Four-Electrode System.

| Voltage 2[a] | pH 2 | Voltage 3 | pH 3 | Average pH[b] | Color Expected | Color Observed |
|---|---|---|---|---|---|---|
| 300 | 8.95 | 280 | 9.02 | 8.985 | Blue | Blue |
| 480 | 8.32 | 460 | 8.39 | 8.355 | Blue-green | Blue-green |
| 660 | 7.69 | 640 | 7.76 | 7.725 | Green-blue | Green-blue |
| 920 | 6.78 | 900 | 6.85 | 6.815 | Green | Green |
| 1100 | 6.15 | 1080 | 6.22 | 6.185 | Yellow | Yellow |
| 1320 | 5.38 | 1300 | 5.45 | 5.415 | Orange-yellow | Orange-yellow |
| 1480 | 4.82 | 1460 | 4.89 | 4.855 | Orange | Orange |
| 1620 | 4.33 | 1600 | 4.4 | 4.365 | Orange-red | Orange-red |
| 1780 | 3.77 | 1760 | 3.84 | 3.805 | Red | Red |

[a]Voltage 1 = 2000; pH 1 = 3; pH ground = 10.
[b]pH = pH ground − pH range × voltage/(total voltage)

Example 4

Monitoring Mobilization of a Focused Protein Band

Figure 6:
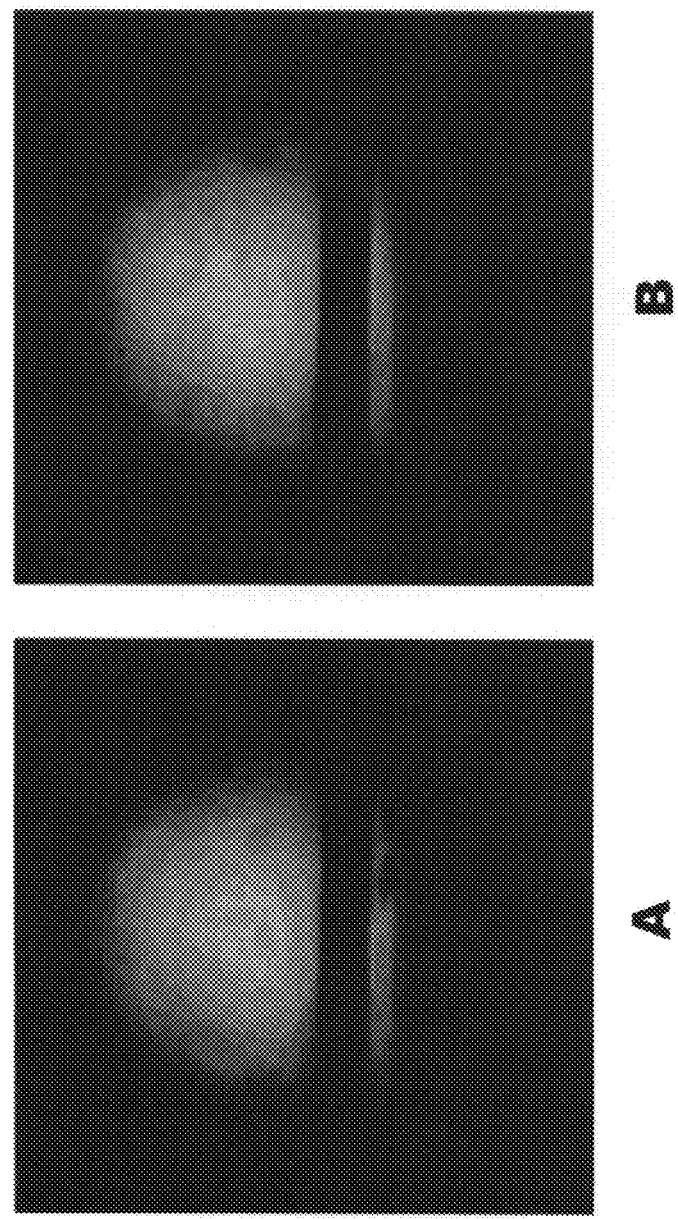
FIG. 6 presents images of a focused protein band during mobilization at time=0 (A), 15 (B), 250 (C), and 300 (D) sec. The microscope viewing area was moved ~1.5 cm for the final two images so that the refocused protein would be within the viewing window.
Figure 6:
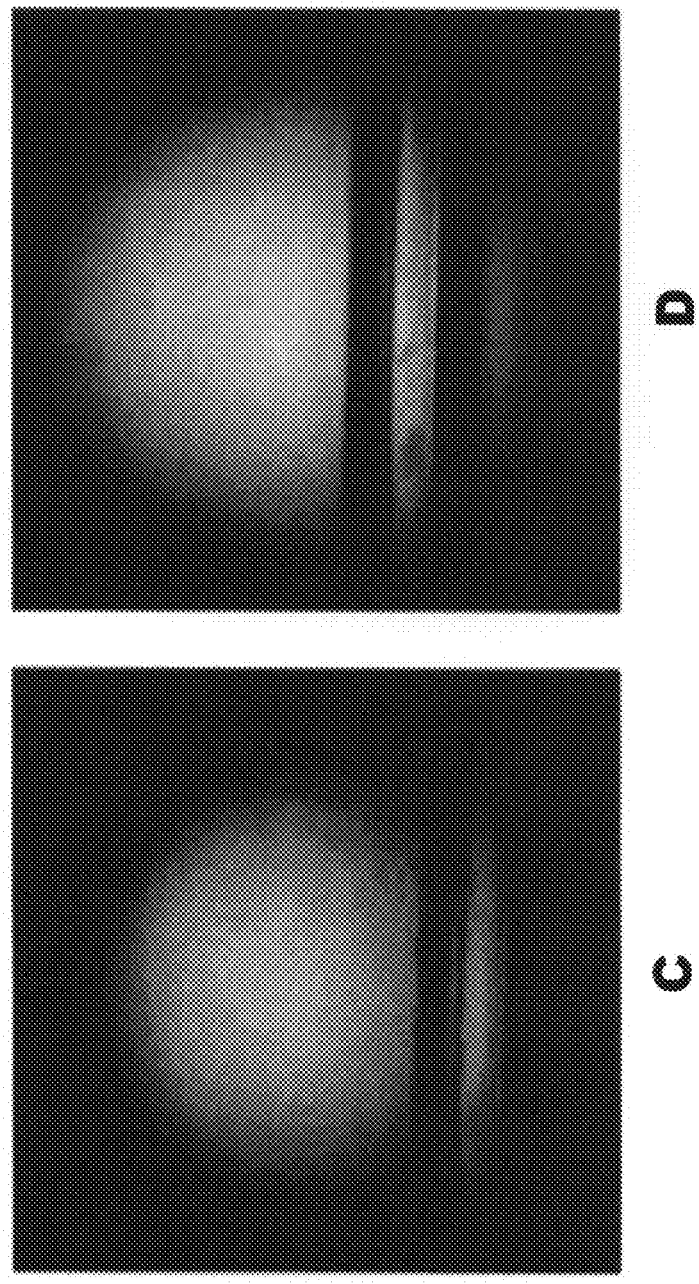

A more direct validation of dynamic IEF was achieved by analyzing a protein and directly viewing the mobilization of a focused protein band. This was performed using an inverted microscope and a fluorescently labeled set of proteins that had a wide range of pI values. FIG. 6A-D shows one of the proteins, horse heart myoglobin, before, during, and after mobilization. The images show the focused, immobile protein (FIG. 6A), the protein moving out of the view window (FIG. 6B), the protein slowing down as it reaches a new position (FIG. 6C), and the protein refocused ~1.5 cm from where it started (FIG. 6D). Note that the viewing window was moved between the second and third frames, and that the width of the protein band was the same before and after mobilization. Although it is difficult to get an accurate measurement of the bandwidth, the 75-μm internal diameter of the capillary gives an estimate of 125 μm. The protein experienced a constant electric field of 40 V/cm, so with a total system voltage of 1 kV, the estimated peak capacity was over 1000.

Example 5

Multidimensional Separation Using Dynamic IEF

To demonstrate dynamic IEF in a simple multidimensional separation, the analytes in the center section of the capillary were collected and analyzed by matrix-assisted laser desorption ionization mass spectrometry (MALDI-MS). This basic setup remained a four-electrode system as described above, with the primary difference being that the capillary section between voltages 1 and 2 was initially filled with a sample of 1 mg/mL horse heart myoglobin in phosphate-buffered saline solution with 1% ampholyte. After focusing was finished, the liquid in the center section was removed, mixed with CHCA matrix and spotted onto a MALDI target. This permitted identification of the analyte present in the center section under various focusing voltages. By monitoring the changes in focused proteins under different conditions, an estimation of the minimum peak capacity could be obtained. For example, if the voltages were changed by 1% of the total system voltage and there was a different protein focused within the center section, then the peak capacity was at least 100. The actual peak capacity would still not be known, but a lower limit could be found.

Figure 7A:
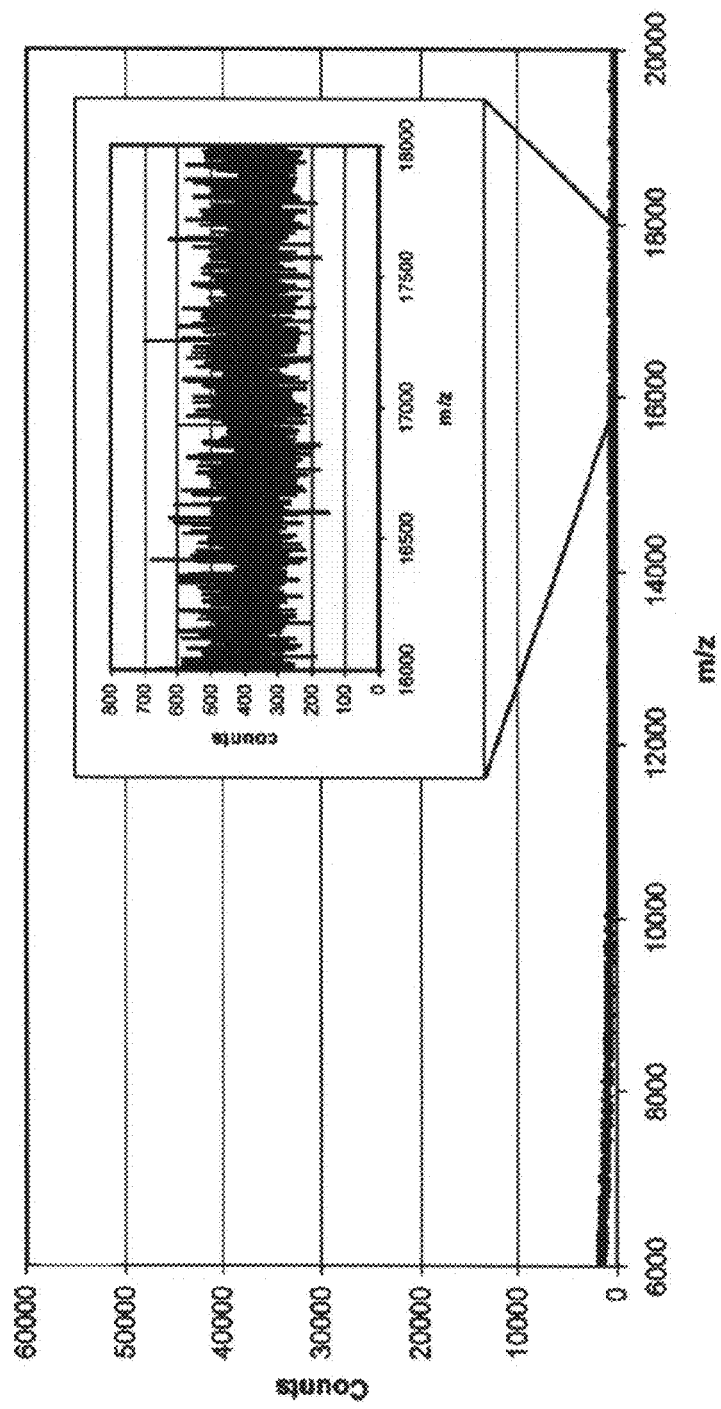
FIG. 7 presents MALDI mass spectra of the contents of the center of the device in a four-electrode system. Panel (A) was focused at voltages of 2200, 1002, 992, 0; and panel (B) was focused at voltages of 2200, 1004, 994, 0. The myoglobin peak at 16 964 m/z is undetectable under the first conditions and has over 50 000 counts under the second conditions.
Figure 7B:
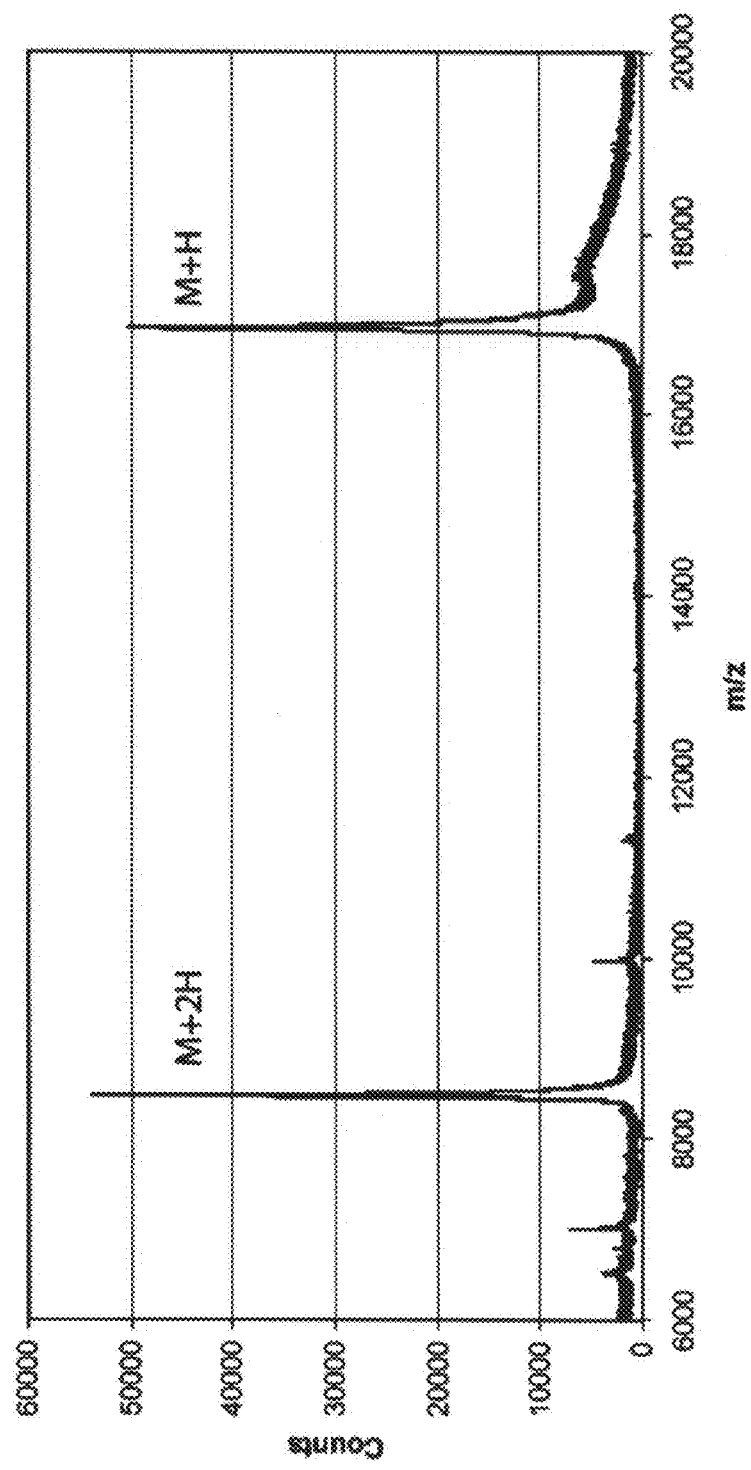

FIG. 7a shows the mass spectrum with voltages of 2200, 1002, and 992 V. The myoglobin peak was absent. When both of the center voltages were increased by 2 V, to 1004 and 994 V, the spectrum in 7b was obtained, showing a strong myoglobin peak. This experiment was repeated four times to demonstrate reproducibility. The replicates with the lower voltage setting did not have a detectable myoglobin peak either individually or with the spectra combined. The higher voltage setting produced myoglobin peaks with average intensities of 40 000 counts and a S/N of >250. This result indicates that at least part of the myoglobin peak was present within the center section after a voltage change of <0.1% of the total voltage. When the center voltages were increased a little more, the myoglobin peak did not increase in size (data not shown), indicating that the entire myoglobin peak was completely focused within the center section after the first increase in voltage. This experiment shows that dynamic IEF can provide a peak capacity of at least 1100 and can maintain this when interfaced to a second analysis method. Although the 4-cm length of the capillary section that is removed limits the attainable resolution of this setup, it does illustrate the great potential of dynamic IEF.

Example 6

Combining Isoelectric Focusing with Fluorescent Anisotropy to Detect Protein Binding Interactions Dynamic IEF is able to fractionate a complex sample into more than one thousand fractions with little or no overlap between the proteins in each fraction. Adjustment of the electrical field permits the collection of focused protein bands without distortion. Coupling dynamic IEF with fluorescence anisotropy provides a means to identify proteins in a complex sample that bind a molecule of interest. Fluorescence anisotropy is a spectroscopic method based on polarization that has been widely used to study molecular interactions, and, in particular, protein binding interactions. This method, termed dynamic isoelectric/anisotropy binding ligand assay (DIABLA), is based upon the isoelectric focusing of proteins in the presence of a fluorescent analyte. The analyte will be uniformly distributed throughout the capillary. Regions that contain a protein bound to the analyte will exhibit a large anisotropy value, whereas the anisotropy will approach zero in regions without protein or with proteins that do not interact with the test compound. The concept of DIABLA was first tested using capillary IEF and fluorescence anisotropy.

Experimental Methods

Chemicals. Acetic acid, ammonium acetate, hydroxypropyl cellulose (HPC, avg. MW 100,000), HPLC grade dimethylsulfoxide (DMSO), HPLC grade water, BSA, and phosphate buffered saline (PBS, pH 7.4) were obtained from Fisher Scientific (Fairlawn, N.J.). Ampholytes (Pharmolyte 3-10 for IEF) were obtained from Amersham Biosciences (Piscataway, N.J.). Tetramethylrhodamine-5-(and 6)-isothiocyanate (TRITC), a fusion protein containing the ligand binding domain (LBD) of the human progesterone receptor and fluorescein-labeled progesterone (Fluormone™ PL Green) were obtained from Invitrogen (Carlsbad, Calif.).

Sample Preparation. TRITC-labeled proteins were prepared according to manufacturer's protocol. Briefly, BSA was dissolved in water to a final concentration of 6 μg/mL, and the LBD of the progesterone receptor was dissolved in PBS to a final concentration of 3 μg/mL. TRITC was dissolved in DMSO at 1 mg/mL. The TRITC solution was added to the protein sample, and incubated in the dark for 2 hours.

Focusing Capillaries. 75 μm i.d., 360 μm o.d. fused silica capillaries (Polymicro, Phoenix, Ariz.) were coated with hydroxypropyl cellulose (HPC) by filling the capillaries with a 5% HPC solution and then baking them at 200° C. for 45 minutes. This treatment effectively eliminated the electroosmotic flow in the capillary.

cIEF. The high voltage power supply used was fabricated in-house. It contains five 10 kV supplies (Ultravolt, Ronkonkoma, N.Y., each of which is individually controlled by a computer using software written in LabView (National Instruments, Austin, Tex.). The catholyte consisted of 0.2 M acetic acid and the anolyte was 0.5% ammonium hydroxide in water. A 10 cm section of coated capillary was cut and the polyimide was removed from a 4 cm section in the center of the capillary. This capillary was then filled with a buffer of the sample (containing the two proteins and the fluorescent progesterone) and 1% carrier ampholytes prior to analysis.

Fluorescence anisotropy. Fluorescence emission was viewed using a Leica inverted microscope with a 10× long range objective in an epifluorescence configuration. Excitation for the TRITC tagged proteins was at 544 nm with emission at 572 nm. Excitation for the fluorescein tagged progesterone was at 494 nm with emission at 520 nm. A polarization filter was used for anisotropy measurements and a digital video camera was attached to the microscope for recording images and video.

Results

Figure 8:
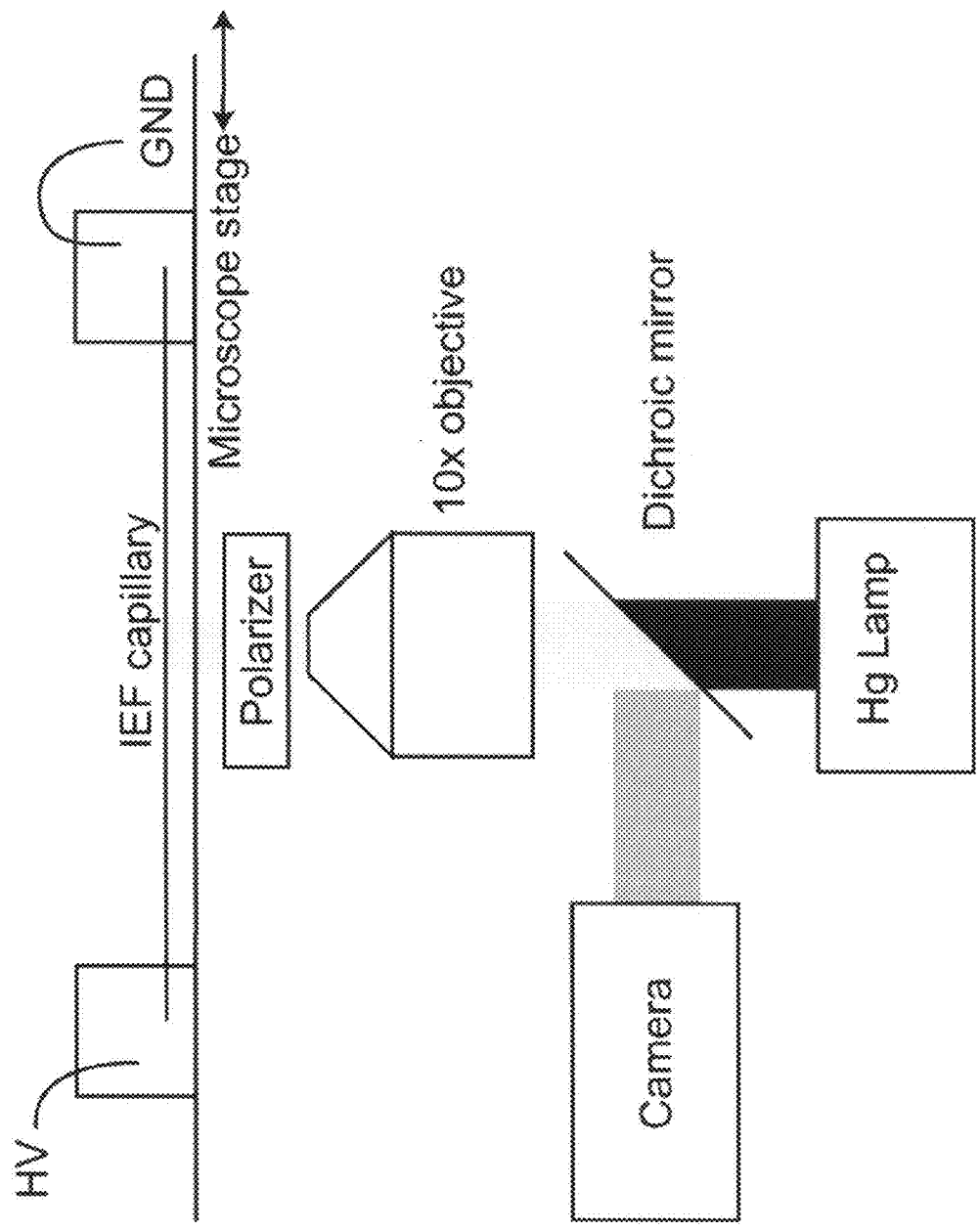
FIG. 8 depicts a diagram of a capillary isoelectric focusing-fluorescence anisotropy system in the epifluorescence mode.

The configuration of the cIEF system integrated onto the stage of the fluorescent microscope is as shown in FIG. 8. Since the microscope was operated in epifluorescence mode, it was not possible to measure a true anisotropy value. Instead, a polarizer was placed between the microscope objective and the capillary, as illustrated. Since the fluorescent progesterone in free solution had an anisotropy value close to zero, it only emitted a small amount of light having the same polarization as the excitation and only was faintly visible. When it was bound to a protein, however, its anisotropy was greater than zero, causing it to be very bright. Since both the parallel and perpendicular emission intensities were not measured, the anisotropy value could be calculated, but this configuration did permit the detection of areas with increased anisotropies.

To test protein-ligand interactions using this system, a progesterone ligand binding assay was performed, using BSA as a reference protein to compare binding affinities. The capillary was filled with a solution containing ~100 nM of each labeled protein, 100 nM of the fluorescein labeled progesterone, and 1% ampholytes, and the proteins were focused at 300V.

FIG. 9A presents a schematic of the results of the experiment. The progesterone ligand was distributed uniformly throughout the capillary, and the two proteins, BSA and the LBD of the progesterone receptor, were focused according to their isoelectric points. TRITC fluorescence confirmed the presence of the two bands of focused protein (FIG. 9B). Fluorescein fluorescent anisotropy revealed the location of where progesterone was bound to the protein, which was at the same position in the capillary as the progesterone receptor (FIG. 9C). FIG. 9D presents the anisotropy measurements along the capillary. The region containing the focused BSA band displayed no or low anisotropy, whereas the region containing the progesterone ligand/receptor complex displayed high anisotropy.

Figure 10:
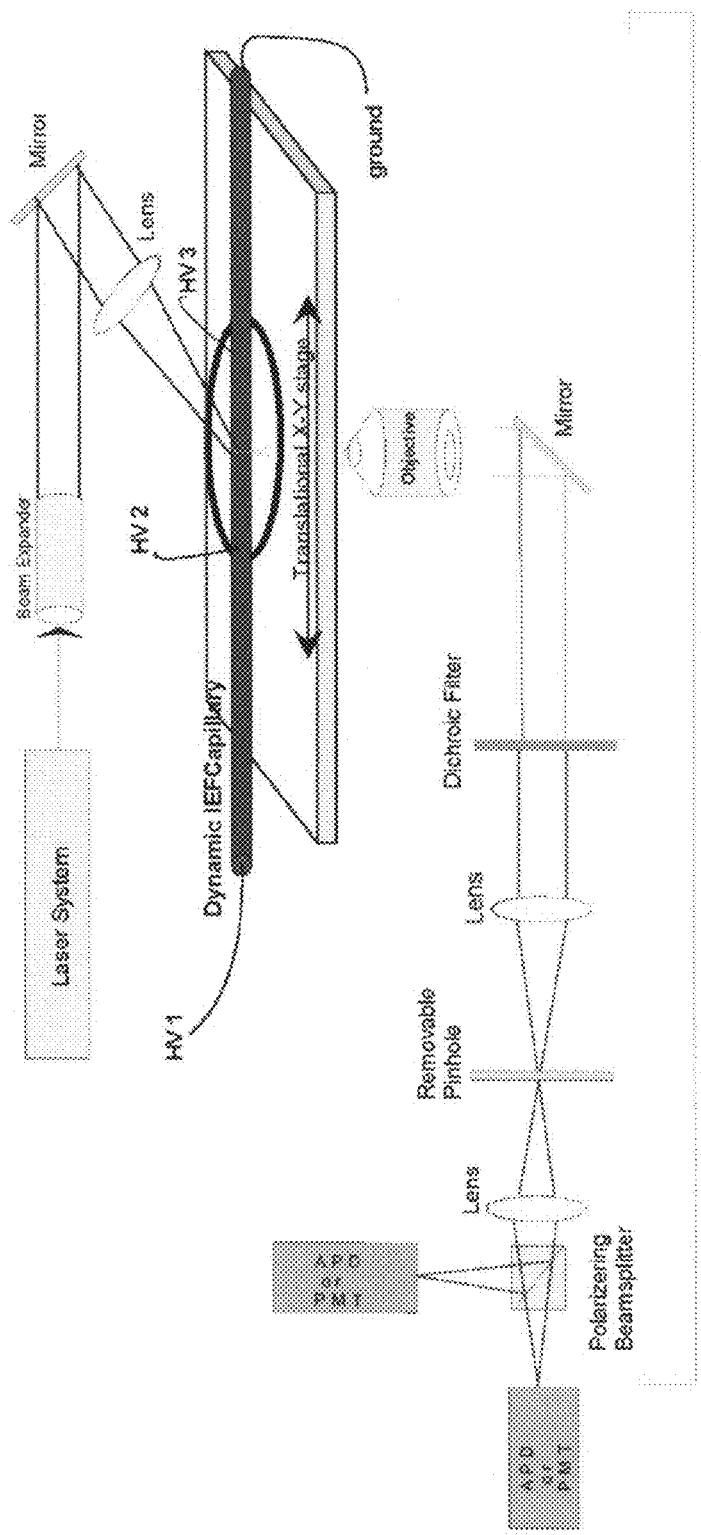
FIG. 10 depicts a schematic representation of an apparatus combining dynamic IEF and fluorescence anisotropy screening.

Thus, this method may be used to rapidly separate and identify proteins that bind a particular analyte. Once a binding interaction has been identified, it would be desirable to collect that protein for additional analyses. Thus, dynamic isoelectric/anisotropy binding ligand assay (DIABLA) would be a powerful analytical tool. A basic setup for DIABLA is illustrated in FIG. 10.

Example 7

Protein Binding Interactions in a Complex Sample

Figure 11:
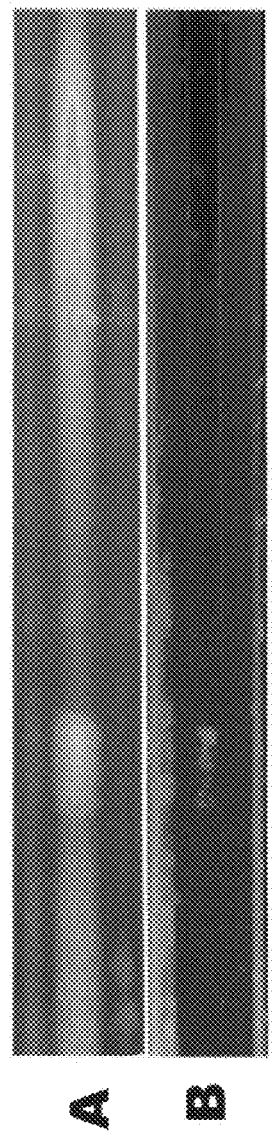
FIG. 11 the anisotropy response between progesterone and proteins in a cell lysate. Panel (A) shows focused protein bands and panel (B) shows a protein bound to of the fluorescein-labeled ligand.

The detection sensitivity of DIABLA was tested by examining progesterone-protein interactions in a lysate from MCF-7 breast cancer cells. The experimental protocols were essentially as described above in Example 6, except that a cell lysate was used rather than pure proteins. Five different protein targets that interact with progesterone were identified. FIG. 11 presents one of the targets. FIG. 11A shows focused proteins in the cell lysate, and FIG. 11B reveals the location of the progesterone bound to a protein in the breast cancer cell lysate. This experiment reveals that DIABLA may be used with complex biological samples.

What is claimed is:

1. A method for detecting an interaction between an analyte and at least one biomolecule, the method comprising:
   a. introducing the analyte and a sample comprising at least one biomolecule into a separation system comprising a device comprising a first electrode at one end of the device and a second electrode at the opposite end of the device;
   b. establishing an electrical field between the first and second electrodes such that a pH gradient forms and each biomolecule in the sample migrates to a position within the gradient that is equal to its isoelectric point, the analyte being distributed throughout the device; and
   c. determining the anisotropy along the length of the device, wherein a non-zero anisotropy value at a particular position along the length of the device indicates the presence of a complex formed between the analyte and the biomolecule that migrated to that position.

2. The method of claim 1, wherein the analyte is fluorescent.

3. The method of claim 1, wherein the device further comprises a solution of ampholytes.

4. The method of claim 1, wherein the device is selected from the group consisting of a capillary, a channel, and a microchannel.

5. The method of claim 1, wherein the sample is selected from the group consisting of a blood sample, a serum sample, a cell lysate, and a tumor cell lysate.

6. The method of claim 1, wherein analyte-biomolecule complex is selected from the group consisting of a ligand and a receptor, a substrate and an enzyme, a pharmaceutical composition and a target that interacts with the pharmaceutical composition, an antigen and an antibody, and a nucleic acid and a nucleic acid binding protein.

7. The method of claim 1, wherein the device comprises at least one additional electrode located between the first and second electrodes, and the separation system comprises at least two high-voltage power sources.

8. The method of claim 7, wherein the device comprises two additional electrodes located between the first and second electrodes, and the separation system comprises three high-voltage power sources.

9. The method of claim 8, further comprising manipulating the position of the analyte-biomolecule complex by adjusting the current applied through the two additional electrodes to change the shape of the electric field and to change the shape of the pH gradient.

10. The method of claim 9, wherein the device further comprises a collection port located between the two additional electrodes.

11. The method of claim 10, wherein the analyte-biomolecule complex is positioned over the collection port by adjusting the current applied through the two additional electrodes.

12. The method of claim 11, wherein the electrical field gradient between the two additional electrodes is low, and the strength of the electric field between the two additional electrodes is low.

13. The method of claim 12, wherein the analyte-biomolecule complex is removed from the device through the collection port.

14. The method of claim 13, wherein the biomolecule of the complex is identified by a method selected from the group consisting of liquid chromatography, gas chromatography, ion mobility spectrometry, mass spectrometry, matrix-assisted laser desorption ionization mass spectrometry, electrospray ionization mass spectrometry, and a combination thereof.

* * * * *